US008148086B2

(12) United States Patent
Zetter et al.

(10) Patent No.: US 8,148,086 B2
(45) Date of Patent: Apr. 3, 2012

(54) METHODS TO PREDICT AND PREVENT RESISTANCE TO TAXOID COMPOUNDS

(75) Inventors: Bruce R. Zetter, Wayland, MA (US); Sabarni K. Chatterjee, Salem, MA (US)

(73) Assignee: Children's Medical Center Corporatioin, Boston, MA (US)

( * ) Notice: Subject to any disclaimer, the term of this patent is extended or adjusted under 35 U.S.C. 154(b) by 287 days.

(21) Appl. No.: 12/085,125

(22) PCT Filed: Nov. 17, 2006

(86) PCT No.: PCT/US2006/044819

§ 371 (c)(1),
(2), (4) Date: Jun. 29, 2009

(87) PCT Pub. No.: WO2007/061922

PCT Pub. Date: May 31, 2007

(65) Prior Publication Data

US 2009/0312405 A1 Dec. 17, 2009

Related U.S. Application Data

(60) Provisional application No. 60/737,653, filed on Nov. 17, 2005.

(51) Int. Cl.
*G01N 33/53* (2006.01)
*G01N 33/574* (2006.01)

(52) U.S. Cl. ........................................ 435/7.1; 435/7.23

(58) Field of Classification Search ........................ None
See application file for complete search history.

(56) References Cited

U.S. PATENT DOCUMENTS

2006/0275810 A1* 12/2006 Georges et al. .................... 435/6
2007/0122830 A1* 5/2007 Georges et al. .................... 435/6

OTHER PUBLICATIONS

Dell'Orco et al (The Breast Journal, 1997, 3:85-89, abstract only) 1 page.*
Dell'Orco et al (The Breast Journal, 1997, 3:85-89).*
Chumbalkar et al (Proteomics, Mar. 2005, 5:1167-1177).*

* cited by examiner

*Primary Examiner* — Laura B Goddard
(74) *Attorney, Agent, or Firm* — Wolf, Greenfield & Sacks, P.C.

(57) ABSTRACT

Embodiments of the invention are directed to methods for predicting the resistance of cancer to members of the taxoid family by measuring the levels of prohibitin. Methods for treating cancer and taxoid family member resistant cancers using inhibitors of prohibitin, as well as therapeutic complexes that target prohibitin are also provided.

9 Claims, 7 Drawing Sheets

MES-SA MES-SA-DX5 A549 A549-TR

GST-π

GAPDH maakvfesig kfglalavag gvvnsalynv daghravifd rfrgvqdivv gegthflipw vqkpiifdcr srprnvpvit
gskdlqnvni tlrilfrpva sqlpriftsi gedydervlp sitteilksv varfdageli tqrelvsrqv sddlteraat fglilddvsl
thltfgkeft eaveakqvaq qeaerarfvv ekaeqqkkaa iisaegdska aelianslat agdglielrk leaaediayq
lsrsmityl pagqsvllql pq (SEQ ID NO:1)

FIG. 5

1 agtatgtgtg gttggggaat tcatgtggag gtcagagtgg aagcaggtgt gagagggtcc
61 agcagaagga aacatggctg ccaaagtgtt tgagtccatt ggcaagtttg gcctggcctt
121 agctgttgca ggaggcgtgg tgaactctgc cttatataat gtggatgctg ggcacagagc
181 tgtcatcttt gaccgattcc gtggagtgca ggacattgtg gtaggggaag ggactcattt
241 tctcatcccg tgggtacaga aaccaattat ctttgactgc cgttctcgac cacgtaatgt
301 gccagtcatc actggtagca aagatttaca gaatgtcaac atcacactgc gcatcctctt
361 ccggcctgtc gccagccagc ttcctcgcat cttcaccagc atcggagagg actatgatga
421 gcgtgtgctg ccgtccatca caactgagat cctcaagtca gtggtggctc gctttgatgc
481 tggagaacta atcacccaga gagagctggt ctccaggcag gtgagcgacg accttacaga
541 gcgagccgcc acctttgggc tcatcctgga tgacgtgtcc ttgacacatc tgaccttcgg
601 gaaggagttc acagaagcgg tggaagccaa acaggtggct cagcaggaag cagagagggc
661 cagatttgtg gtggaaaagg ctgagcaaca gaaaaaggcg gccatcatct ctgctgaggg
721 cgactccaag gcagctgagc tgattgccaa ctcactggcc actgcagggg atggcctgat
781 cgagctgcgc aagctggaag ctgcagagga catcgcgtac cagctctcac gctctcggaa
841 catcacctac ctgccagcgg ggcagtccgt gctcctccag ctgcccccagt gagggcccac
901 cctgcctgca cctccgcggg ctgactgggc cacagccccg atgattctta acacagcctt
961 ccttctgctc ccaccccaga aatcactgtg aaatttcatg attggcttaa agtgaaggaa
1021 ataaaggtaa aatcacttca gatctctaat tagtctatca aatgaaactc tttcattctt
1081 ctcacatcca tctacttttt tatccacctc cctaccaaaa attgccaagt gcctatgcaa
1141 accagcttta ggtcccaatt cggggcctgc tggagttccg gcctgggcac cagcatttgg
1201 cagcacgcag gcggggcagt atgtgatgga ctggggagca caggtgtctg cctagatcca
1261 cgtgtggcct ccgtcctgtc actgatggaa ggtttgcgga tgagggcatg tgcggctgaa
1321 ctgagaaggc aggcctccgt cttcccagcg gttcctgtgc agatgctgct gaagagaggt
1381 gccggggagg ggcagagagg aagtggtctg tctgttacca taagtctgat tctctttaac
1441 tgtgtgacca gcggaaacag gtgtgtgtga actgggcaca gattgaagaa tctgcccctg
1501 ttgaggtggg tgggcctgac tgttgccccc cagggtccta aaacttggat ggacttgtat
1561 agtgagagag gaggcctgga ccgagatgtg agtcctgttg aagacttcct ctctaccccc
1621 caccttggtc cctctcagat acccagtgga attccaactt gaaggattgc atcctgctgg
1681 ggctgaacat gcctgccaaa gacgtgtccg acctacgttc ctggccccct cgttcagaga
1741 ctgcccttct cacgggctct atgcctgcac tgggaaggaa acaaatgtgt ataaactgct
1801 gtcaataaat gacacccaga ccttcc (SEQ ID NO:7)

FIG. 6

METHODS TO PREDICT AND PREVENT RESISTANCE TO TAXOID COMPOUNDS

CROSS REFERENCE

This application is a national stage filing under 35 U.S.C. §371 of PCT International application PCT/US2006/044819 designating the United States of America, filed Nov. 17, 2006, which claims the benefit under 35 U.S.C. §119(e) of U.S. provisional application Ser. No. 60/737,653, filed Nov. 17, 2005, both of which are incorporated herein by reference.

GOVERNMENT SUPPORT

This invention was supported, in part, by National Institutes of Health (NIH) Grant No. R37CA37393. The government of the United States has certain rights to the invention.

BACKGROUND OF THE INVENTION

Members of the taxoid family of compounds, e.g. docetaxel and paclitaxel, have potent anti-tumor activities (Wang et al., Cancer 88:2619, 2000, (5,6,7)). Docetaxel inhibits microtubule dynamics by binding to beta-tubulin and blocking disassembly of alpha- and beta-tubulin heterodimers thus abrogating tumor growth. Paclitaxel (Taxol™) is a complex diterepene derived from the Pacific yew tree *Taxus brevifolia* (1) that also has significant anti-tumor activity. Paclitaxel primarily suppresses microtubule dynamics and interferes with spindle formation arresting cell cycle at mitosis leading to apoptosis (6,7).

The clinical use of taxoid compounds has expanded to include cancers of the breast, ovaries and lung (2-4) and is expected to expand further. As with many cancer therapeutic agents, resistance to taxoid family members remains a significant hindrance in their application as a successful chemotherapeutic drugs. Resistance to the taxoid compounds can be either inherent or acquired subsequent to treatment most likely due to emergence of a minority population. For example, Paclitaxel resistance is believed to be a multifactorial phenomenon. The principle mechanisms underlying resistance include the overexpression of transporter protein P-glycoprotein, altered binding of paclitaxel to its cellular target, β-tubulin, mutations in the β-tubulin gene, overexpression of β-tubulin isotypes, and decreased sensitivity to apoptotic stimuli. The role of P-glycoprotein as a potential mediator of resistance has been abundantly studied. Several P-glycoprotein inhibitors have been characterized although relatively few of these, such as verapamil and cyclosporine, have shown any clinical efficacy and are frequently accompanied by dose-limiting side effects. Recently, there has been renewed effort to find novel effectors of drug resistance which could provide alternative strategies for resistance reversal.

SUMMARY OF INVENTION

We have undertaken a systematic proteomic approach to identify novel proteins associated with resistance to taxoid compounds (e.g. paclitaxel and docetaxel) and to examine their potential use as targets for modulating the resistant phenotype. We have identified prohibitin as a protein that modulates sensitivity to the taxoid family member paclitaxel, as well as determined that multi-drug resistant cell lines have elevated levels of prohibitin on their cell surface relative to cell lines that are sensitive to taxoid compounds. We have further confirmed a role for GST-π in paclitaxel resistance (17) and demonstrate that it is possible to reverse paclitaxel resistance in vitro by simultaneously silencing prohibitin and GST-π. Identification of prohibitin as a modulator of resistance to taxoid family members has important diagnostic and therapeutic implications for patients whose cancers are resistant to therapy with taxoid compounds.

Methods for predicting resistance of cancer to a member of the taxoid family in a subject are provided. In one embodiment, the level of prohibitin in a biological sample obtained from the subject is measured and compared to a standard level, wherein an elevation of the measured level of prohibitin relative to the standard level is indicative of resistance to a member of the taxoid family.

In one embodiment, a method for predicting the resistance of cancer in a subject to a member of the taxoid family is provided that comprises measuring the level of prohibitin in multiple biological samples obtained from a subject periodically over a period time; and measuring a change in the measured level of prohibitin in the biological samples. An elevation of the measured level of prohibitin over time is indicative of resistance to a member of the taxoid family.

Methods for improving the effectiveness of cancer treatment are also provided. In one embodiment, the level of prohibitin in a biological sample is measured, wherein an elevated level of prohibitin as compared to a standard level indicates that the subject is resistant to treatment with a member of the taxoid family and is in need of alternative treatment thereby improving the effectiveness of cancer treatment.

In one embodiment, the biological sample is blood, tissue, serum, plasma, urine, stool, cerebrospinal fluid, nipple aspirates, tumor biopsy, or cell lysate. In one embodiment, the subject has previously been treated with a member of the taxoid family, e.g. paclitaxel or docetaxel. In one embodiment, serial monitoring of the level of prohibitin is performed at least quarterly, at least bimonthly, at least biweekly, at least weekly, at least every three days or at least daily.

In one embodiment, in methods of the invention, the level of prohibitin is measured by measuring the level of prohibitin on the cell surface of cancer cells in the biological sample.

In one embodiment, in methods of the invention, the biological sample is a cell lysate and the level of prohibitin is measured by measuring the level of prohibitin in the microsomal fraction of the biological sample.

In one embodiment, in methods of the invention, the biological sample is serum and the level of prohibitin is determined by measuring the level of prohibitin in the serum.

In one embodiment, in methods of the invention, the biological sample is blood and the level of prohibitin is determined by measuring the level of prohibitin in platelets of the blood sample.

In one embodiment, in methods of the invention, the level of prohibitin protein is measured using an antibody-based binding moiety which specifically binds prohibitin. The antibody-based binding moiety can be labeled with a detectable label, for example a radioactive label, a hapten label, a fluorescent label, and an enzymatic label. In one embodiment, the antibody-based binding moiety is an antibody, e.g. a monoclonal antibody.

In one embodiment, in methods of the invention, the level of prohibitin protein is measured using Western Blot analysis, Fluorescent activated cell sorting (FACS), enzyme-linked immunosorbent assay (ELISA), immunohistochemistry, mass spectrometry, radio-immunoassay, surface plasmon resonance, or immunofluorescence.

Other embodiments of the invention provide methods for treating cancers that are resistant to a taxoid family member.

In one embodiment, a method of treating a cancer is provided in which the subject is administered an inhibitor of prohibitin. In one embodiment, the cancer is resistant to a taxoid family member. In another embodiment, the subject is administered a taxoid family member. In one embodiment, the taxoid family member is paclitaxel. In one embodiment, the inhibitor of prohibitin inhibits translocation of prohibitin to the cell surface. In another embodiment, the inhibitor of prohibitin inhibits transcription or expression of prohibitin. In one embodiment, the inhibitor of prohibitin is selected from an siRNA, antibody, small molecule, or peptide. In one embodiment, an inhibitor of glutathione-S-transferase π and an inhibitor of prohibitin are administered.

In another embodiment a method of treating a cancer that is resistant to a taxoid family member is provided. In the method, an agent that selectively binds prohibitin is bound to a therapeutic agent and administered to a subject.

In one embodiment, the therapeutic agent is a drug, a chemotherapeutic agent, a radioisotope, a pro-apoptosis agent, an anti-angiogenic agent, a hormone, a cytokine, a cytotoxic agent, a cytocidal agent, a peptide, a protein, an antibiotic, an antibody, a Fab fragment of an antibody, a hormone antagonist, or an antigen.

In one embodiment, the agent that selectively binds prohibitin is a peptide having the amino acid sequence of CKGGEAKDC (SEQ ID NO:2).

In one embodiment, the agent is an antibody-based binding moiety.

Articles of manufacture comprising the prohibitin inhibitors and therapeutic agents of the invention are also provided.

In other aspects of the invention, methods to direct treatment of a subject are provided. In one embodiment, the method comprises having a subject tested for the level of prohibitin in a biological sample, wherein a clinician reviews the results as compared to a standard level of prohibitin, and if the biological sample has an elevated level of prohibitin as compared to a standard level the clinician directs the subject to be treated with a compound comprising an agent that selectively binds prohibitin and a therapeutic agent. The test may be performed in the same country where the subject resides or in another country and the results are made available, for example via a Web site, or are transmitted to the clinician.

In another embodiment, the method comprises having a subject tested for the level of prohibitin in a biological sample, wherein a clinician reviews the results as compared to a standard level of prohibitin, and if the biological sample has an elevated level of prohibitin as compared to a standard level the clinician directs the subject to be treated with a inhibitor of prohibitin. The test may be performed in the same country where the subject resides or in another country and the results are made available, for example via a Web site, or are transmitted to the clinician.

BRIEF DESCRIPTION OF THE DRAWINGS

FIG. 2A, Western blot on the cytoplasmic fractions of MES-SA and MES-SA DX5 (left panel) and A549 and A549TR (right panel) using GST-π antibodies. FIG. 2B, Western blot on microsomal fractions of MES-SA and MES-SA DX5 (left panel) and A549 and A549TR (right panel) using prohibitin antibodies. FIG. 2C, Western blot on whole cell lysates of MES-SA and MES-SA DX5 (left panel) and A549 and A549TR (right panel) using GST-π antibodies. FIG. 2D, Western blot on whole cell lysates of MES-SA and MES-SA DX5 (left panel) and A549 and A549TR (right panel) using prohibitin antibodies. Equivalent loading was demonstrated using GAPDH and actin. Protein samples were prepared as described in the two-dimensional electrophoresis studies.

FIG. 3A, GST-π siRNA (Smartpool), and FIG. 3B, Prohibitin siRNA (Smartpool) transfected A549-TR cells were treated with or without Paclitaxel 24 h after transfection. Cell survival was analyzed after 72 h of Paclitaxel treatment by cell counting. Proteins were extracted for western blot at the same time. Percent cell survival was calculated as percentage of cell survival in GST-π and prohibitin siRNA transfected cells compared to cells transfected by a negative control siRNA. (Inset): Western blot analysis confirms knockdown of respective protein at the end of the assay time (96 h). Each bar is SD from a representative experiment done in at least in duplicates.

FIG. 4 A, A549TR cells and FIG. 4B, MES-SA DX5 cells were transfected with siRNA for GST-π and prohibitin in combination, 24 h after cells were seeded. Cells were then treated with or without Paclitaxel 24 h after siRNA transfection. Cell survival was analyzed after 72 h of paclitaxel treatment by cell counting. Proteins were extracted for Western blotting at the same time. Percent cell survival was calculated by comparing number of cells in GST-π and prohibitin siRNA transfected cells compared to number of cells transfected by a negative control siRNA. Each bar represents the SD from a representative experiment performed at least in duplicates.

FIG. 5 shows the protein sequence of *Homo Sapiens* prohibitin (SEQ ID NO:1).

FIG. 6 shows the nucleic acid sequence of *Homo Sapiens* prohibitin (SEQ ID NO:7).

DESCRIPTION OF THE INVENTION

Figure 1A:
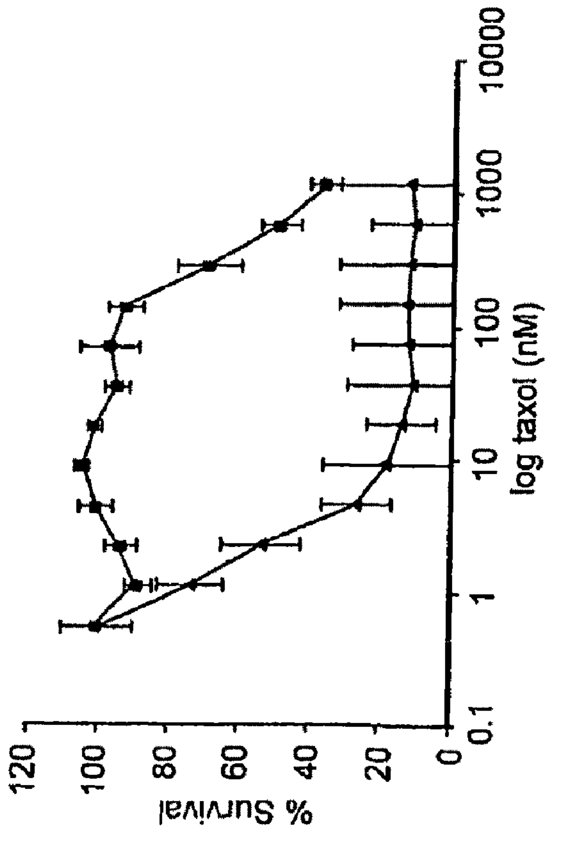
FIGS. 1A and 1B show graphs illustrating the effect of paclitaxel on cell proliferation. A549 and A549 TR cell lines (FIG. 1A) and MES-SA and MES-SA-DX5 cell lines (FIG. 1B) were treated with various concentrations of paclitaxel. 24 hours after $1\times10^4$ cells/well were seeded in 96 well plates. MTT assay for cell survival was performed 72 h after paclitaxel addition. X axis: concentration of paclitaxel, Y axis-% survival.
Figure 1B:
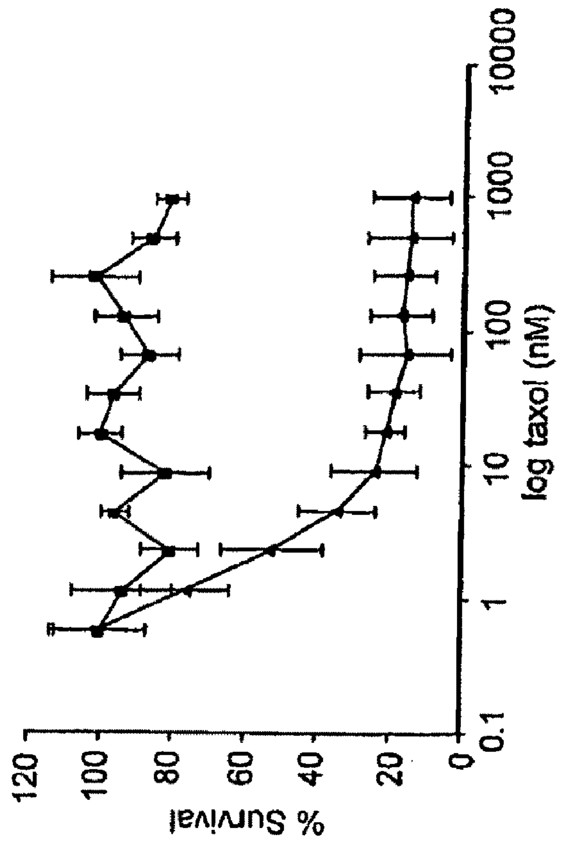

Embodiments of the present invention are directed to methods for predicting the resistance of cancer to members of the taxoid family by measuring the levels of prohibitin. Methods for treating cancer and taxoid family member resistant cancers are also provided.

As used herein, the term “a taxoid family member” or “taxoid compound” refers to a class of chemotherapeutic compounds belonging to the taxane family. Specific members of the taxoid family include, but are not limited, to paclitaxel (Taxol™), docetaxel (Taxotere™) and analogs thereof (i.e., XRP9881 and XRP6258; see Ojima and Geney, Curr Opin Investig Drugs 4:73 7, 2004). This class of molecules are β-tubulin binders and stabilize the polymerized form of the microtubule. “A taxoid family member resistant cancer” refers to a cancer that is not sensitive to the taxoid family compounds, i.e. the cancer does not respond to the anti-cancer effects of the compounds.

As used herein, a “cancer” in a subject or patient refers to the presence of cells possessing characteristics typical of cancer-causing cells, such as uncontrolled proliferation, immortality, metastatic potential, rapid growth and proliferation rate, and certain characteristic morphological features.

Often, cancer cells will be in the form of a tumor, but such cells may exist alone within a subject, or may be a non-tumorigenic cancer cell, such as a leukemia cell. In some circumstances, cancer cells will be in the form of a tumor; such cells may exist locally within an animal, or circulate in the blood stream as independent cells, for example, leukemic cells. Examples of cancer include but are not limited to breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer. In one embodiment, the cancer is not a lipoma.

As used herein, a "biological sample" refers to a sample of biological material obtained from a patient, preferably a human patient, including a tissue, a tissue sample, a cell sample, e.g., a tissue biopsy, such as, an aspiration biopsy, a brush biopsy, a surface biopsy, a needle biopsy, a punch biopsy, an excision biopsy, an open biopsy, an incision biopsy or an endoscopic biopsy), and a tumor sample. Biological samples can also be biological fluid samples, including but not limited to, urine, blood, serum, platelets, saliva, cerebrospinal fluid, nipple aspirates, and cell lysate (e.g. supernatant of whole cell lysate, microsomal fraction, membrane fraction, or cytoplasmic fraction). The sample may be obtained using any methodology known to one skilled in the art. Methods for platelet extraction are found in PCT publication WO 2005/103281.

Embodiments of the invention also encompasses the use of isolates of a biological sample in the methods of the invention. As used herein, an "isolate" of a biological sample (e.g., an isolate of a tissue or tumor sample) refers to a material or composition (e.g., a biological material or composition) which has been separated, derived, extracted, purified or isolated from the sample and preferably is substantially free of undesirable compositions and/or impurities or contaminants associated with the biological sample.

As used herein, a "tissue sample" refers to a portion, piece, part, segment, or fraction of a tissue which is obtained or removed from an intact tissue of a subject, preferably a human subject.

In one embodiment, the biological sample is treated as to prevent degradation of protein. Methods for inhibiting or preventing degradation include, but are not limited to, treatment of the biological sample with protease, freezing the biological sample, or placing the biological sample on ice. Preferably, prior to analysis, the biological samples or isolates are constantly kept under conditions as to prevent degradation of protein, e.g. prohibitin.

As used herein "serially monitoring" a level of prohibitin in a sample, refers to measuring a level of prohibitin in a sample more than once, e.g., quarterly, bimonthly, monthly, biweekly, weekly, every three days or daily. Serial monitoring of a level includes periodically measuring a level of prohibitin at regular intervals as deemed necessary by the skilled artisan.

A used herein, the term "subject" or "patient" refers generally to a mammal.

As used herein, "Prohibitin" refers to the Prohibitin protein of Genebank accession NP_002625 (*Homo sapiens*) (SEQ ID NO:1) (FIG. 5). The term also encompasses species variants, homologues, allelic forms, mutant forms, and equivalents thereof.

The term "antagonist" or "inhibitor" is used in the broadest sense, and includes any molecule that partially or fully blocks, inhibits, or neutralizes a biological activity of prohibitin or the transcription or translation thereof. Suitable antagonist molecules specifically include antagonist antibodies or antibody fragments, fragments, peptides, small organic molecules, anti-sense nucleic acids, siRNA, etc.

The term "standard level" as used herein refers to a baseline amount of prohibitin as determined in one or more normal subjects that does not have a cancer resistant to a taxoid family member. For example, a baseline may be obtained from at least one subject and preferably is obtained from an average of subjects (e.g., n=2 to 100 or more), wherein the subject or subjects have no prior history of resistance to a taxoid family member. A baseline standard level can also be derived from taxoid family member sensitive cell lines, a cell that is not resistant to a taxoid family member.

As used herein, the term "standard level" is also intended to include a baseline amount of prohibitin as determined in the subject that is to be monitored for taxoid family member resistance. For example, one need not directly compare the amount of prohibitin in a subject's sample to a standard level derived from normal subjects, rather one can measure a change in concentration of prohibitin present in multiple biological samples obtained from the subject over a period of time, e.g. the standard level used for comparison is the level of prohibitin measured in the first biological sample obtained from the subject. An elevation in the measured concentration of prohibitin over a period of time is indicative of resistance to a member of the taxoid family.

As used herein, "a period of time" is intended to include a period of days, weeks, months or even years. Multiple biological samples are obtained from a subject over a period of time, i.e. a biological sample is obtained from a subject periodically over time at various intervals. A biological sample can be obtained from a subject at any interval. For example, a biological sample can be taken every day for weeks, months or years. Alternatively, a biological sample can be obtained once a week, twice a week, three times a week, four times a week, five times a week, or six times a week for a period of weeks, months or years. In one embodiment, a biological sample is obtained once a week over a period of three months. In one embodiment, a biological sample is obtained once a month for a period of months, or years.

For purposes of comparison, the level of prohibitin in a biological sample to be measured is of the same type (obtained from the same biological source) as what is used for determination of the baseline standard level. For example, in one embodiment of the invention, the level of prohibitin is measured by measuring the level of prohibitin on the cell surface of cancer cells in the biological sample. Thus, the baseline standard level is determined by measuring the level of prohibitin on the cell surface of non-resistant cancer cells. Alternatively, the biological sample is a cell lysate and the level of prohibitin is measured by measuring the level of prohibitin in the microsomal fraction of the biological sample. Thus, the baseline standard level is determined by measuring the level of prohibitin in the microsomal fraction of the biological sample obtained from non-resistant cancer cells. Means for isolation of the microsomal fraction from cells are well known to those skilled in the art.

In one embodiment, the biological sample is serum and the level of prohibitin is determined by measuring the level of prohibitin in the serum. Thus, the baseline standard level is determined by measuring the level of prohibitin in serum from a subject that does not have a taxoid family member resistant cancer.

In one embodiment, the biological sample is blood and the level of prohibitin is determined by measuring the level of prohibitin in platelets of the blood sample. Thus, the baseline standard level is determined by measuring the level of prohibitin in platelets from a subject that does not have a taxoid family member resistant cancer.

As used herein, "elevation" of a measured level of prohibitin relative to a standard level means that the amount or concentration of prohibitin in a sample is sufficiently greater in a subject's biological sample relative to the standard level of prohibitin. For example, elevation of the measured level relative to a standard level may be any statistically significant elevation which is detectable. Such an elevation may include, but is not limited to, about a 1%, about a 10%, about a 20%, about a 40%, about an 80%, about a 2-fold, about a 4-fold, about an 8-fold, about a 20-fold, or about a 100-fold elevation, or more, relative to the standard. The term "about" as used herein, refers to a numerical value plus or minus 10% of the numerical value.

In one embodiment, the methods of the invention may be performed concurrently with methods of detection for other analytes, e.g., detection of mRNA or protein of other markers associated with taxoid family resistance (e.g. P-glycoprotein, β-tubulin, mutations in the β-tubulin gene, or overexpression of β-tubulin isotypes).

Measuring Levels of Prohibitin

The level of prohibitin protein can be measured by any means known to one skilled in the art including, but not limited to, competition binding assays, mass spectrometry, Western blot, fluorescent activated cell sorting (FACS), enzyme-linked immunosorbent assay (ELISA), antibody arrays, high pressure liquid chromatography, optical biosensors, and surface plasmon resonance.

In one embodiment, prohibitin protein is detected by contacting the biological sample with an antibody-based binding moiety that specifically binds to prohibitin, or to a fragment of that protein. Formation of the antibody-protein complex is then detected and measured to indicate protein levels. Anti-prohibitin antibodies are available commercially (e.g. human prohibitin affinity purified polyclonal and monoclonal Ab's from R&D Systems, Inc. Minneapolis, Minn. 55413; AVIVA Systems Biology, San Diego, Calif. 92121; see also U.S. Pat. No. 5,463,026 Antibodies Alternatively, antibodies can be raised against the full length prohibitin, or a portion of prohibitin.

Antibodies for use in the present invention can be produced using standard methods to produce antibodies, for example, by monoclonal antibody production (Campbell, A. M., Monoclonal Antibodies Technology: Laboratory Techniques in Biochemistry and Molecular Biology, Elsevier Science Publishers, Amsterdam, the Netherlands (1984); St. Groth et al., J. Immunology, (1990) 35: 1-21; and Kozbor et al., Immunology Today (1983) 4:72). Antibodies can also be readily obtained by using antigenic portions of the protein to screen an antibody library, such as a phage display library by methods well known in the art. For example, U.S. Pat. No. 5,702,892 (U.S.A. Health & Human Services) and WO 01/18058 (Novopharm Biotech Inc.) disclose bacteriophage display libraries and selection methods for producing antibody binding domain fragments.

The term "antibody-based binding moiety" or "antibody" includes immunoglobulin molecules and immunologically active determinants of immunoglobulin molecules, e.g., molecules that contain an antigen binding site which specifically binds (immunoreacts with) prohibitin. The term "antibody-based binding moiety" is intended to include whole antibodies, e.g., of any isotype (IgG, IgA, IgM, IgE, etc), and includes fragments thereof which are also specifically reactive with prohibitin, or fragments thereof. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's may be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled.

"Labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS.

In the methods of the invention that use antibody based binding moieties for the detection of profilin, the level of the protein of interest present in the biological samples correlate to the intensity of the signal emitted from the detectably labeled antibody.

In one preferred embodiment, the antibody-based binding moiety is detectably labeled by linking the antibody to an enzyme. The enzyme, in turn, when exposed to it's substrate, will react with the substrate in such a manner as to produce a chemical moiety which can be detected, for example, by spectrophotometric, fluorometric or by visual means. Non-limiting examples of enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. Chemiluminescence is another method that can be used to detect an antibody-based binding moiety.

Detection may also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by audoradiography. Isotopes which are particularly useful for the purpose of the present invention are $^{3}H$, $^{131}I$, $^{35}S$, $^{14}C$, and preferably $^{125}I$.

It is also possible to label an antibody with a fluorescent compound. When the fluorescently labeled antibody is exposed to light of the proper wave length, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}Eu$, or others of the lanthanide series. These metals can be attached to the antibody using such metal chelating groups as diethylenetriaminepentaacetic acid (DTPA) or ethylenediaminetetraacetic acid (EDTA).

The levels of prohibitin, in the biological samples, can be measured by immunoassays, such as enzyme linked immunoabsorbant assay (ELISA), radioimmunoassay (RIA), Immunoradiometric assay (IRMA), Western blotting, or immunohistochemistry, each of which are described in more detail below. In one embodiment, the presence of cell surface prohibitin is measured using FACS analysis, competition binding assays, or RIA/IRMA. Antibody arrays or protein chips can also be employed, see for example U.S. Patent Application Nos: 20030013208A1; 20020155493A1; 20030017515 and U.S. Pat. Nos. 6,329,209; 6,365,418, which are herein incorporated by reference in their entirety.

Immunoassays

"Radioimmunoassay (RIA)" is a technique for detecting and measuring the concentration of an antigen using a labeled, e.g. radioactively labeled, form of the antigen. Examples of radioactive labels for antigens include $^{3}H$, $^{14}C$, and $^{125}I$. The concentration of antigen, e.g., prohibitin, in a biological sample is measured by having the antigen in the biological sample compete with the labeled, e.g. radioactively, antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." ELISA is a technique for detecting and measuring the concentration of an antigen using a labeled, e.g., enzyme linked, form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody, e.g. antibodies against prohibitin, is linked to a solid phase, i.e. a microtiter plate, and exposed to a biological sample containing antigen, prohibitin The solid phase is then washed to remove unbound antigen. A labeled antibody, e.g. enzyme linked, is then bound to the bound-antigen, if present, forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen, e.g., prohibitin. The antigen-antibody mixture is then contacted with a solid phase, e.g. a microtiter plate, that is coated with antigen, e.g., prohibitin. The more antigen present in the sample, the less free antibody that will be available to bind to the solid phase. A labeled, e.g., enzyme linked, secondary antibody is then added to the solid phase to determine the amount of primary antibody bound to the solid phase.

Alternatively, prohibitin levels in cells and/or tumors can be detected in vivo in a subject by introducing into the subject a labeled antibody to prohibitin protein. For example, the antibody can be labeled with a radioactive marker whose presence and location in a subject can be detected by standard imaging techniques.

In one embodiment, immunohistochemistry ("IHC") and immunocytochemistry ("ICC") techniques are used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of a specific antibody, wherein antibodies are used to specifically target molecules inside or on the surface of cells. The antibody typically contains a marker that will undergo a biochemical reaction, and thereby experience a change color, upon encountering the targeted molecules. In some instances, signal amplification may be integrated into the particular protocol, wherein a secondary antibody, that includes the marker stain, follows the application of a primary specific antibody. Immunoshistochemical assays are known to those of skill in the art (e.g., see Jalkanen, et al., J. Cell. Biol. 101:976-985 (1985); Jalkanen, et al., J. Cell. Biol. 105:3087-3096 (1987).

Typically, for immunohistochemistry, tissue sections are obtained from a patient and fixed by a suitable fixing agent such as alcohol, acetone, and paraformaldehyde, to which is reacted an antibody. Conventional methods for immunohistochemistry are described in Harlow and Lane (eds) (1988) In "Antibodies A Laboratory Manual", Cold Spring Harbor Press, Cold Spring Harbor, N.Y.; Ausbel et al (eds) (1987), in Current Protocols In Molecular Biology, John Wiley and Sons (New York, N.Y.). Biological samples appropriate for such detection assays include, but are not limited to, cells, tissue biopsy, whole blood, plasma, serum, sputum, cerebrospinal fluid, pleural fluid, urine and the like.

For direct labeling techniques, a labeled antibody is used. For indirect labeling techniques, the sample is further reacted with a labeled substance.

Alternatively, immunocytochemistry may be used. In general, cells are obtained from a patient and fixed by a suitable fixing agent such as alcohol, acetone, and paraformaldehyde, to which is reacted an antibody. Methods of immunocytological staining of human samples is known to those of skill in the art and described, for example, in Brauer et al., 2001 (FASEB J, 15, 2689-2701), Smith-Swintosky et al., 1997.

Immunological methods of the present invention are advantageous because they require only small quantities of biological material. Such methods may be done at the cellular level and thereby necessitate a minimum of one cell. Preferably, several cells are obtained from a subject.

Other techniques may be used to detect the levels of prohibitin according to a practitioner's preference, based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. In one embodiment, western blotting is used to detect levels of prohibitin in the microsomal fraction of cell lysate. Detectably labeled antibodies can then be used to detect and/or assess levels of the prohibitin protein where the intensity of the signal from the detectable label corresponds to the amount of protein. Levels can be quantitated, for example by densitometry.

Mass Spectometry

In addition, prohibitin levels may be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of a marker or other substances will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands, any of the components of a mass spectrometer, e.g., desorption source, mass analyzer, detect, etc., and varied sample preparations can be combined with other suitable components or preparations described herein, or to those known in the art. For example, in some embodiments a control sample may contain heavy atoms, e.g. $^{13}C$, thereby permitting the test sample to mixed with the known control sample in the same mass spectrometry run.

In one preferred embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to provide better quantify the amount of the biomolecule present in the first sample. In certain embodiments, the identity of the biomolecules in the first and second sample can also be determined.

In one embodiment of the invention, levels of prohibitin are detected by MALDI-TOF mass spectrometry.

Methods of detecting prohibitin in a biological samples also include the use of surface plasmon resonance (SPR). In such assays an antibody the binds prohibitin need not be detectably labeled and can be used without a second antibody that binds to the specific polypeptide. For example, an antibody specific for prohibitin may be bound to an appropriate solid substrate and then exposed to the sample. Binding of a prohibitin to the antibody on the solid substrate may be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). Optical biosensors are also contemplated for use in embodiments of the invention.

The SPR biosensing technology has been combined with MALDI-TOF mass spectrometry for the desorption and identification of biomolecules. In a chip-based approach to BIA-MS, a ligand, e.g., prohibitin antibody, is covalently immobilized on the surface of a chip. Proteins from a sample are routed over the chip, and the relevant are bound by the ligand. After a washing step, the eluted proteins are analyzed by MALDI-TOF mass spectrometry. The system may be a fully automated process and is applicable to detecting and characterizing proteins present in complex biological fluids and cell extracts at low- to subfemtomol levels.

Methods of Treatment

The invention further encompasses a method for improving the effectiveness of cancer treatment in a subject with cancer. The method comprises measuring the level of prohibitin in a biological sample, wherein an elevated level of prohibitin as compared to a standard level indicates that a subject is resistant to treatment with a member of the taxoid family and is need of an alternative treatment so as to improve the effectiveness of cancer treatment.

In one embodiment the method comprises serially monitoring a level of prohibitin in a sample obtained from the subject during a period of treatment with a taxoid family member; and comparing the level measured to a standard level, wherein elevation of the measured level of relative to the standard level indicates that the subject is in need of additional treatment.

In one embodiment, a method for treating cancer a is provided wherein the patient is administered an inhibitor of prohibitin. In one embodiment, the cancer is a taxoid family member resistant cancer. The patient may be administered a taxoid family member compound concurrently, prior to, or subsequent to administration of a prohibitin inhibitor. In one embodiment, the patient is administered an additional compound or agent that reverses taxoid family member resistance (e.g. inhibitor of glutathione-S-transferase $\pi$, inhibitor of p-glycoprotein etc.) and/or is administered a compound or agent that has anti-cancer activity.

The inhibitor can prevent the accumulation at any step of the pathway from the gene to protein activity, e.g. preventing transcription, reducing mRNA levels, preventing translation, or inhibiting the protein itself, e.g. inhibiting translocation of prohibitin to the cell surface, or inhibiting prohibitin at the cell surface. Such inhibitors can include antibodies, small molecules (drugs or compounds), antisense molecules, siRNA, ribozymes, repressors of gene transcription, or competitive or non-competitive molecular inhibitors of the gene product art.

In one embodiment, prohibitin inhibitor is administered to subject who does not have a taxoid family member resistant cancer. Means for determining taxoid family member resistance and sensitivity are well known to those skilled in the In one embodiment, treatment may involve a combination of treatments, including, but not limited to a prohibitin inhibitor in combination with chemotherapy, radiation, or drugs/agents known to be effective against cancer.

In connection with the administration of a prohibitin inhibitor or other anti-cancer agent, a drug which is "effective against" a cancer indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

The term "drug" or "compound" or "agent" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

Compounds that specifically target prohibitin, whether detected in vivo or in vitro, can be selected using techniques known in the art and discussed herein. Candidate drug screening assays may be used to identify bioactive candidate agents that inhibit the activity of prohibitin. Of particular interest are screening assays for agents that have a low toxicity for human cells. A wide variety of assays may be used for this purpose, including labeled in vitro protein-protein binding assays, electrophoretic mobility shift assays, enzyme activity assays, immunoassays for protein binding, and the like. Purified profiling may also be used for determination of three-dimensional crystal structure, which can be used for modeling intermolecular interactions, transporter function, etc. Such compounds may be, for example, small molecules, antibodies, aptamers, siRNAs, and vectors that inhibit prohibitin activity which confers resistance to a taxoid family member.

In one embodiment, compounds useful in the method of the present invention are antibodies which interfere prohibitin activity, including monoclonal, chimeric humanized, and recombinant antibodies and fragments thereof which are characterized by their ability to inhibit the taxoid family member resistance activity of prohibitin and which have low toxicity.

Neutralizing antibodies are readily raised in animals such as rabbits or mice by immunization with prohibitin. Immunized mice are particularly useful for providing sources of B cells for the manufacture of hybridomas, which in turn are cultured to produce large quantities of anti-prohibitin monoclonal antibodies. Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined. Humanized antibodies are immunoglobin molecules created by genetic engineering techniques in which the murine constant regions are replaced with human counterparts while retaining the murine antigen binding regions. The resulting mouse-human chimeric antibody should have reduced immunogenicity and improved pharmacokinetics in humans.

In one embodiment, an antisense strategy may be used to interfere with the taxoid resistance activity of prohibitin. This approach may, for instance, utilize antisense nucleic acids or ribozymes that block translation of a specific mRNA, either by masking that mRNA with an antisense nucleic acid or cleaving it with a ribozyme. For a general discussion of antisense technology, see, e.g., Antisense DNA and RNA, (Cold Spring Harbor Laboratory, D. Melton, ed., 1988).

Reversible short inhibition of prohibitin gene transcription may also be useful. Such inhibition can be achieved by use of siRNAs. RNA interference (RNAi) technology prevents the expression of genes by using small RNA molecules such as small interfering RNAs (siRNAs). This technology in turn takes advantage of the fact that RNAi is a natural biological mechanism for silencing genes in most cells of many living organisms, from plants to insects to mammals (McManus et al., Nature Reviews Genetics, 2002, 3(10) p. 737). RNAi prevents a gene from producing a functional protein by ensuring that the molecule intermediate, the messenger RNA copy of the gene is destroyed. siRNAs can be used in a naked form and incorporated in a vector, as described below. One can further make use of aptamers to specifically inhibit variant FTase gene transcription, see, for example, U.S. Pat. No. 6,699,843. Aptamers useful in the present invention may be identified using the SELEX process. The methods of SELEX have been described in, for example, U.S. Pat. Nos. 5,707,796, 5,763,177, 6,011,577, 5,580,737, 5,567,588, and 5,660,985. The nucleic acid sequence of human Prohibitin is found in Genebank at NM_002634.

The siRNAs may be chemically synthesized, produced using in vitro transcription, etc. SiRNAs have been described in Brummelkamp et al., Science 296; 550-553, 2002, Jaque et al., Nature 418; 435-438, 2002, Elbashir S. M. et al. (2001) Nature, 411: 494-498, McCaffrey et al. (2002), Nature, 418: 38-39; Xia H. et al. (2002), Nat. Biotech. 20: 1006-1010, Novina et al. (2002), Nat. Med. 8: 681-686, and U.S. Application No. 20030198627.

The delivery of siRNA to tumors can potentially be achieved via any of several gene delivery "vehicles" that are currently available. These include viral vectors, such as adenovirus, lentivirus, herpes simplex virus, vaccinia virus, and retrovirus, as well as chemical-mediated gene delivery systems (for example, liposomes), or mechanical DNA delivery systems (DNA guns). The oligonucleotides to be expressed for such siRNA-mediated inhibition of gene expression would be between 18 and 28 nucleotides in length.

An "antisense nucleic acid" or "antisense oligonucleotide" is a single stranded nucleic acid molecule, which, on hybridizing under cytoplasmic conditions with complementary bases in a RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes, RNAi, aptamers and Rnase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

In one embodiment, the administered inhibitor may be an antisense oligonucleotides, particularly synthetic oligonucleotides; having chemical modifications from native nucleic acids, or nucleic acid constructs that express such anti-sense molecules as RNA. The antisense sequence is complementary to the mRNA of the prohibitin gene, and inhibits expression of the targeted gene products (see e.g. Nyce et al. (1997) Nature 385:720). Antisense molecules inhibit gene expression by reducing the amount of mRNA available for translation, through activation of RNAse H or steric hindrance. One or a combination of antisense molecules may be administered, where a combination may comprise multiple different sequences from a single targeted gene, or sequences that complement several different genes. Generally, the antisense sequence will have the same species of origin as the animal host, species variants of prohibitin are available in Genebank e.g., mouse NM_008831.3, NP_032857; Rat NM_031851.2, NP_114039. Antisense molecules may be produced by expression of all or a part of the target gene sequence in an appropriate vector, where the vector is introduced and expressed in the targeted cells. The transcriptional initiation will be oriented such that the antisense strand is produced as an RNA molecule.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it (Cech, 1989, Science 245(4915) p. 276). Because they are sequence-specific, only mRNAs with particular sequences are inactivated.

Aptamers are also useful. Aptamers are a promising new class of therapeutic oligonucleotides or peptides and are selected in vitro to specifically bind to a given target with high affinity, such as for example ligand receptors. Their binding characteristics are likely a reflection of the ability of oligonucleotides to form three dimensional structures held together by intramolecular nucleobase pairing. Aptamers are synthetic DNA, RNA or peptide sequences which may be normal and modified (e.g. peptide nucleic acid (PNA), thiophosphorylated DNA, etc) that interact with a target protein, ligand (lipid, carbohydrate, metabolite, etc). In a further embodiment, RNA aptamers specific for prohibitin can be introduced into or expressed in a cell as a therapeutic.

Peptide nucleic acids (PNAs) are compounds that in certain respects are similar to oligonucleotides and their analogs and thus may mimic DNA and RNA. PNA'S are suitable inhibitors for use in embodiments of the invention. In PNA, the deoxyribose backbone of oligonucleotides has been replaced by a pseudo-peptide backbone (Nielsen et al. 1991 Science 254, 1457-1500). Each subunit, or monomer, has a naturally occurring or non-naturally occurring nucleobase attached to this backbone. One such backbone is constructed of repeating units of N-(2-aminoethyl) glycine linked through amide bonds. PNA hybridises with complementary nucleic acids through Watson and Crick base pairing and helix formation. The Pseudo-peptide backbone provides superior hybridization properties (Egholm et al. Nature (1993) 365, 566-568), resistance to enzymatic degradation (Demidov et al. Biochem. Pharmacol. (1994) 48, 1310-1313) and access to a variety of chemical modifications (Nielsen and Haaima Chemical Society Reviews (1997) 73-78). PNAs specific for a variant FTase can be introduced into or expressed in a cell as a therapeutic. PNAs have been described, for example, in U.S. Application No. 20040063906.

Once identified, such inhibitor compounds are administered to patients in need of taxoid resistance treatment, for example, patients affected with or at risk for developing taxoid resistance.

The route of administration of inhibitors or other therapeutic compounds/complexes of the invention may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like. The therapeutic compounds/compositions of the invention can be administered parenterally by injection or by gradual infusion over time and can be delivered by peristaltic means.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the invention are formulated into conventional oral administration forms such as capsules, tablets and tonics.

For topical administration, the pharmaceutical composition (inhibitor of kinase activity) is formulated into ointments, salves, gels, or creams, as is generally known in the art.

The therapeutic compositions of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

Any formulation or drug delivery system containing the therapeutic, which is suitable for the intended use, as are generally known to those of skill in the art, can be used. Suitable pharmaceutically acceptable carriers for oral, rectal, topical or parenteral (including inhaled, subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

Patients to be treated with a compound which inhibits or targets prohibitin include, for example, patients diagnosed with taxoid family member resistance, patients who initially respond to therapy with a taxoid family member, but subsequently fail to respond to the same or similar compound. Compounds can be combined that target multiple proteins involved in taxoid family member resistance.

Another embodiment of the invention provides methods of treating subjects with taxoid family member resistant cancers. In particular, taxoid family member resistant cancers with elevated levels of prohibitin on the cell surface of cancer cells. The method comprises administering a compound that comprises and agent that selectively binds prohibitin and a therapeutic agent.

In one embodiment, the agent that selectively binds prohibitin is a peptide.

As used herein, a "protein" or "peptide" generally refers, but is not limited to, a protein of greater than about 200 amino acids up to a full length sequence translated from a gene; a polypeptide of about 100 to 200 amino acids; and/or a "peptide" of from about 3 to about 100 amino acids. For convenience, the terms "protein," "polypeptide" and "peptide" are used interchangeably herein.

As used herein, an "amino acid" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

The agent that selectively binds prohibitin (e.g. the targeting protein or peptide) can be attached to a therapeutic agent to form a complex. For example, this can be done by the generation of fusion proteins. Such molecules generally have all or a substantial portion of the targeting peptide (i.e. the protein or peptide that selectively binds prohibitin), linked at the N- or C-terminus, to a portion of a second polypeptide or protein (i.e. therapeutic agent). Examples of proteins or peptides that may be incorporated into a fusion protein with the peptide or protein that selectively binds prohibitin include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually any protein or peptide could be incorporated into a fusion protein comprising a targeting peptide that selectively binds prohibitin. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

Alternatively, the agent that selectively bind prohibitin may be attached to therapeutic agents using a variety of known cross-linking agents. Methods for covalent or non-covalent attachment of proteins or peptides are well known in the art. Such methods may include, but are not limited to, use of chemical cross-linkers, photoactivated cross-linkers and/or bifunctional cross-linking reagents. Exemplary methods for cross-linking molecules are disclosed in U.S. Pat. No. 5,603,872 and U.S. Pat. No. 5,401,511, incorporated herein by reference. Non-limiting examples of cross-linking reagents of potential use include glutaraldehyde, bifunctional oxirane, ethylene glycol diglycidyl ether, carbodiimides such as 1-ethyl-3-(3-dimethylaminopropyl) carbodiimide or dicyclohexylcarbodiimide, bisimidates, dinitrobenzene, N-hydroxysuccinimide ester of suberic acid, disuccinimidyl tartarate, dimethyl-3,3'-dithio-bispropionimidate, azidoglyoxal, N-succinimidyl-3-(2-pyridyldithio)propionate and 4-(bromoadminoethyl)-2-nitrophenylazide.

Homobifunctional reagents that carry two identical functional groups are highly efficient in inducing cross-linking. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied.

In certain embodiments, it may be appropriate to link one or more agents to a liposome or other membrane-bounded particle. For example, targeting peptides or agents and therapeutic agents can be cross-linked to liposomes, microspheres or other such devices may be used to deliver larger volumes of a therapeutic agent to a target organ, tissue or cell type. Various ligands can be covalently bound to liposomal surfaces through the cross-liking of amine residues. Liposomes containing phosphatidylethanolamine (PE) may be prepared by established procedures. The inclusion of PE provides an active functional amine residue on the liposomal surface. In another non-limiting example, heterobifunctional cross-linking reagents and methods of use are disclosed in U.S. Pat. No. 5,889,155, incorporated herein by reference. The cross-linking reagents combine a nucleophilic hydrazide residue with an electrophilic maleimide residue, allowing coupling in one example, of aldehydes to free thiols. The cross-linking reagent can be modified to cross-link various functional groups.

In one embodiment, the peptide that selectively binds prohibitin is CKGGEAKDC SEQ ID NO: 2 (See U.S. Patent Application Publication 2006/0094672).

In one embodiment, the protein or peptide that selectively binds prohibitin is an antibody-based binding moiety.

Other techniques of general use for proteins or peptides that are known in the art have not been specifically disclosed herein, but may be used in the practice of the claimed subject matter.

Therapeutic Agents

Therapeutic agents or factors suitable for attaching to an agent that selectively binds prohibitin may include any chemical compound that induces apoptosis, cell death, cell stasis and/or anti-angiogenesis or otherwise affects the survival and/or growth rate of a cancer cell. Examples of some of these compounds are listed below.

Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-Like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Tsujimoto et al., 1985). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins that share in common structural and sequence homologies. These different family members have been shown to either possess similar functions to Bcl-2 (e.g., Bcl.sub.XL, Bcl.sub.W, Bcl.sub.S, Mcl-1, A1, Bfl-1) or counteract Bcl-2 function and promote cell death (e.g., Bax, Bak, Bik, Bim, Bid, Bad, Harakiri).

Non-limiting examples of pro-apoptosis agents contemplated within the scope of the present invention include gramicidin, magainin, mellitin, defensin, cecropin, $(KLAKLAK)_2$ (SEQ ID NO: 3), $KLAKKLA)_2$ (SEQ ID NO:4), $(KAAKKAA)_2$ (SEQ ID NO:5) or $(KLGKKLG)_3$ (SEQ ID NO:6).

Angiogenic Inhibitors

In certain embodiments the present invention may concern administration of targeting peptides attached to anti-angiogenic agents, such as angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

Proliferation of tumors cells relies heavily on extensive tumor vascularization, which accompanies cancer progression. Thus, inhibition of new blood vessel formation with anti-angiogenic agents and targeted destruction of existing blood vessels have been introduced as an effective and relatively non-toxic approach to tumor treatment. (Arap et al., Science 279:377-380, 1998a; Arap et al., Curr. Opin. Oncol. 10:560-565, 1998b; Ellerby et al., Nature Med. 5:1032-1038, 1999). A variety of anti-angiogenic agents and/or blood vessel inhibitors are known. (E.g., Folkman, In: Cancer: Principles and Practice, eds. DeVita et al., pp. 3075-3085, Lippincott-Raven, New York, 1997; Eliceiri and Cheresh, Curr. Opin. Cell. Biol. 13, 563-568, 2001).

Cytotoxic Agents

A wide variety of anticancer agents are well known in the art and any such agent may be coupled to a cancer targeting peptide for use within the scope of the present invention. Exemplary cancer chemotherapeutic (cytotoxic) agents of potential use include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of (DTIC), transplatinum, vinblastine and methotrexate, vincristine, or any analog or derivative variant of the foregoing. Most chemotherapeutic agents fall into the categories of alkylating agents, antimetabolites, antitumor antibiotics, corticosteroid hormones, mitotic inhibitors, and nitrosoureas, hormone agents, miscellaneous agents, and any analog or derivative variant thereof.

Chemotherapeutic agents and methods of administration, dosages, etc. are well known to those of skill in the art (see for example, the "Physicians Desk Reference", Goodman & Gilman's "The Pharmacological Basis of Therapeutics" and "Remington: The Science and Practice of Pharmacy," 20th edition, Gennaro, Lippincott, 2000, each incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Of course, all of these dosages and agents described herein are exemplary rather than limiting, and other doses or agents may be used by a skilled artisan for a specific patient or application. Any dosage in-between these points, or range derivable therein is also expected to be of use in the invention.

Alkylating Agents

Alkylating agents are drugs that directly interact with genomic DNA to prevent cells from proliferating. This category of chemotherapeutic drugs represents agents that affect all phases of the cell cycle, that is, they are not phase-specific. An alkylating agent, may include, but is not limited to, nitrogen mustard, ethylenimene, methylmelamine, alkyl sulfonate, nitrosourea or triazines. They include but are not limited to: busulfan, chlorarnbucil, cisplatin, cyclophosphamide (cytoxan), dacarbazine, ifosfamide, mechlorethamine (mustargen), and melphalan.

Antimetabolites

Antimetabolites disrupt DNA and RNA synthesis. Unlike alkylating agents, they specifically influence the cell cycle during S phase. Antimetabolites can be differentiated into various categories, such as folic acid analogs, pyrimidine analogs and purine analogs and related inhibitory compounds. Antimetabolites include but are not limited to, 5-fluorouracil (5-FU), cytarabine (Ara-C), fludarabine, gemcitabine, and methotrexate.

Natural Products

Natural products generally refer to compounds originally isolated from a natural source, and identified as having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers.

Antibiotics

Certain antibiotics have both antimicrobial and cytotoxic activity. These drugs also interfere with DNA by chemically inhibiting enzymes and mitosis or altering cellular membranes. These agents are not phase specific so they work in all phases of the cell cycle. Examples of cytotoxic antibiotics include, but are not limited to, bleomycin, dactinomycin, daunorubicin, doxorubicin (Adriamycin); plicamycin (mithramycin) and idarubicin.

Miscellaneous Agents

Miscellaneous cytotoxic agents that do not fall into the previous categories include, but are not limited to, platinum coordination complexes, anthracenediones, substituted ureas, methyl hydrazine derivatives, amsacrine, L-asparaginase, and tretinoin. Platinum coordination complexes include such compounds as carboplatin and cisplatin (cis-DDP). An exemplary anthracenedione is mitoxantrone. An exemplary substituted urea is hydroxyurea. An exemplary methyl hydrazine derivative is procarbazine (N-methylhydrazine, MIH). These examples are not limiting and it is contemplated that any known cytotoxic, cytostatic or cytocidal agent may be attached to targeting peptides and administered to a targeted organ, tissue or cell type within the scope of the invention.

Cytokines and Chemokines

In certain embodiments, it may be desirable to couple specific bioactive agents to one a targeting peptide that selectively binds prohibitin. Such agents include, but are not limited to, cytokines and/or chemokines.

The term "cytokine" is a generic term for proteins released by one cell population that act on another cell as intercellular mediators. Examples of cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-alpha. and -beta; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-.alpha., -.beta., and -.gamma.; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL-9, IL-10, IL-11, IL-12; IL-13, IL-14, IL-15, IL-16, IL-17, IL-18, LIP, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines.

Dosages

The skilled artisan is directed to "Remington: The Science and Practice of Pharmacy," 20th edition, Gennaro, lippincott (2000). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA Office of Biologics standards.

Kits

In another aspect, the invention concerns an article of manufacture or package, comprising a container, a composition within the container comprising a prohibitin antagonist (inhibitor of prohibiting, e.g., an anti-prohibitin antibody, optionally a label on or associated with the container that indicates that the composition can be used for treating a condition characterized by resistance to a taxoid family member, and a package insert containing instructions to administer the antagonist to patients who have been found to have taxoid family member resistance, e.g. elevated levels of prohibitin. A therapeutic product may include sterile saline or another pharmaceutically acceptable emulsion and suspension base.

In another embodiment, the invention provides s an article of manufacture or package, comprising a container, a composition within the container comprising an agent (e.g. protein or peptide) that selectively binds prohibitin, complexed to a therapeutic agent, optionally a label on or associated with the container that indicates that the composition can be used for treating cancer.

Embodiments of the invention are also directed to commercial kits for the detection of levels of prohibitin. The kit can be in any configuration well known to those of ordinary skill in the art and is useful for performing one or more of the methods described herein for the detection of prohibitin. The kits are convenient in that they supply many if not all of the essential reagents for conducting an assay or assays for the detection of prohibitin. In addition, the assay is preferably performed simultaneously with a standard or multiple standards that are included in the kit, such as a predetermined amount of protein so that the results of the test can be quantitated or validated.

The kits include a means for detecting prohibitin protein, such as antibodies, or antibody fragments, which selectively bind to prohibitin. The detection kit can be formulated in a standard two-antibody binding format in which, for example, one specific antibody captures prohibitin in a patient sample and another specific antibody is used to detect captured protein. For example, the capture antibody is immobilized on a solid phase, e.g., an assay plate, an assay well, a nitrocellulose membrane, a bead, a dipstick, or a component of an elution column. The second antibody, i.e., the detection antibody, is typically tagged with a detectable label such as a calorimetric agent or radioisotope.

In other embodiments, the detection kits may employ, but are not limited to, the following techniques: competitive and non-competitive assays, radioimmunoassay (RIA), bioluminescence and chemiluminescence assays, fluorometric assays, sandwich assays, immunoradiometric assays, dot blots, enzyme linked assays including ELISA, microtiter plates, and immunocytochemistry or immunohistochemistry. For each kit the range, sensitivity, precision, reliability, specificity and reproducibility of the assay are established by means well known to those skilled in the art.

In one embodiment, the detection kit may include means for the detection of other biomarkers, e.g., other cancer markers, e.g., other drug resistance markers.

The above described detection kits would further provide instructions for use.

Examples

Materials and Methods

Materials. Paclitaxel was purchased from Sigma-Aldrich, St. Louis, Mo. The drug was prepared as a 5 mM stock in ethanol and stored in aliqouts at −20° C. Working stock solutions were diluted in DMSO and further diluted in culture medium at appropriate concentrations. The IPG strips, criterion gels, ampholytes and Syproruby stain were purchased from Biorad (city). Phenanthroline, Benzamidine, and PMSF were purchased from Sigma-Aldrich. The following antibodies were used: rabbit anti human prohibitin (BioLegend, city CA) mouse anti-human GST-π (BioLegend), GAPDH (Abcam, Cambridge, Mass.), anti-mouse actin (Abcam, Cambridge, Mass.) Alexa Fluor 568 goat anti-mouse IgG and Alexa Fluor 488 anti-rabbit IgG (Molecular Probes, Eugene, Oreg.) mouse anti-human VDAC/Porin (Abcam, Cambridge, Mass.). SiRNA oligonucleotides were purchased as SMARTpool reagents (Dharmacon, Lafayette, Colo.).

Cell Culture. The human non-small cell lung carcinoma cell line A549 and its Paclitaxel-resistant derivative cell lines were cultured in F-12 Ham nutrient mixture (Invitrogren, Carlsbad, Calif.) supplemented with 10% fetal bovine serum (FBS) at 37° C. in a humidified atmosphere with 5% $CO_2$/95% air. The paclitaxel-resistant cell lines were grown under selective pressure (100 nM paclitaxel), then placed in Paclitaxel-free culture medium 5-7 days before experiments were performed. The uterine sarcoma cells (MES-SA) and the multidrug resistant derivative (MES-SA/DX5) were maintained in McCoy's 5A media (ATCC, Rockville, Md.) supplemented with 10% FBS. The drug-resistant MES-SA/DX5 cells (originally selected with doxorubicin) were initially adapted to paclitaxel by stepwise increase of concentration from 5 nM to 100 nM over a 60-day period. They were subsequently routinely grown in 100 nM paclitaxel, which was withdrawn 5-7 days before experiments were performed.

Protein fractionation. To prepare protein fractions for two-dimensional electrophoresis, cells from the parental cell lines and its drug resistant sublines were grown in five 150 mm tissue culture dishes each. When the cells reached confluency (>80%) they were removed by scrapping into $Ca^{++}$/$Mg^{++}$ free PBS, and washed twice with PBS containing protease inhibitors (5 mM phenanthroline, 5 mM benzamidine and 1 mM PMSF). The cells were then resuspended in a hypotonic solution of 50% PBS homogenized in a glass homogenizer with 20 gentle strokes and centrifuged at 355×g for 10 mins. Nuclear proteins were recovered from the pellet by low-speed centrifugation. The supernatant was centrifuged separately at 27,000×g for 45 minutes to separate the microsomes (pellet) from the cytoplasmic components. The nuclear and microsomal pellets were resuspended in 10 mM Tris-HCl buffer containing 150 mM NaCl, 1% Triton X-114 and protease inhibitors (which ones, what concentrations) and incubated on ice for 10 min. The three protein fractions were diluted separately in 10 mM $NH_4HCO_3$ containing 2% CHAPS and concentrated using a Centricon-20 spin column (Millipore, Billerica, Mass.). The protein concentrates were lyophilized and stored at −20° C. prior to two-dimensional electrophoresis. Separate aliquots (10 μl) were prepared for protein quantification.

Two-dimensional Polyacrylamide Gel Electrophoresis (2D-PAGE). The lyophilized protein fractions were dissolved in 2D-PAGE buffer (8M urea, 2% CHAPS, 100 mM DTT and 0.2% ampholytes) at room temperature. The dissolved proteins were rehydrated on dry IPG strips (pH gradient of 4-7 Biorad) for 16 h-24 h at room temperature. The proteins (50 μg) were analyzed by two-dimensional electrophoresis consisting of an isoelectric-focusing (IEF) step followed by electrophoretic separation using a 4-20% gradient criterion gel (Biorad). Gels were stained with SyproRuby fluorescence stain according to the manufacturer's (Biorad) protocol. All samples were run at least twice to ensure reproducibility. Image analysis was performed on a scanner using PDQuest software from Biorad. Only spots that were differentially expressed in the resistant sublines of both lung cancer and uterine sarcoma cell lines were selected for detailed investigation.

In-Gel Trypsin Digestion and Protein Identification by Tandem Mass Spectrometry

Spots of interest were excised with a PDM1.5 manual spot picker (The Gel Company, San Francisco Calif.). The gel plugs were washed in 100 mM ammonium bicarbonate ($NH_4HCO_3$) solution for 1 h and then incubated with 0.5 ml 1:1 mixture of 50 mM $NH_4HCO_3$ and 50% acetonitrile for 30 minutes. Complete dehydration was achieved by incubating the gel plugs with 200 μl of 100% acetonitrile and the gel pieces were dried in a SpeedVac for 20 minutes. For in gel digestion the dried gel particles were rehydrated with a minimal volume of trypsin solution (10 μg/μl in 25 mM $NH_4HCO_3$) and incubated at 37° C. overnight. The digests were extracted with 50% acetonitrile twice and the resulting pooled protein concentrated with a SpeedVac to approximately 10% of the volume. Protein identification was performed using an Ion-Trap tandem mass spectrometer (Maker, City State). Samples were analyzed by nanoflow HPLC micro-electrospray ionization on a Finnigan LCQ ion trap spectrometer (Thermo-Finnigan San Jose, Calif.). A gradient from 95% A to 80% A for 30 min then to 75% A for 15 min and finally to 110% A for 60 min (where A=0.1% formic Acid in water, B=0.1% formic acid in acetonitrile, (Burdick and Jackson)) was run at 200 nl/min over a self packed, flame pulled C-18 integrated column and electrospray emitter into the LCQ Deca. The 100 μm ID×8 cm fused silica column (Polymicro Technologies, *Phoenix* Ariz.) was slurry packed with Magic C18AQ 200 Å, (Michrom BioResources Auburn, Calif.). Spectra were acquired in a data dependent mode throughout the gradient, a full MS scan followed by 3 subsequent ms/ms scans based of the 3 most intense peaks in the previous full scan. CID fragmentation was achieved by collision energy of 35%, the capillary was heated to 150° C. and electro spray voltage was 1.9 KV. Once an ms/ms spectra was obtained two times it was put on an exclusion list for 3 min to allow for lower intensity peptides to be analyzed. Data was analyzed using the Sequest algorithm by searching against the updated non-redundant database from NCBI. Spectra are ranked by X-correlation score.

Western Blots. Proteins in membrane fractions, cytoplasmic fractions or whole cell lysates were resolved by SDS-PAGE electrophoresis and transferred to PVDF membranes. The membranes were blotted for molecules of interest with anti-prohibitin (1:1000), anti-GST-π (1:1000), anti-GAPDH (1:1000) and anti-actin (1:1000) antibodies for at room temperature for 1 hour or overnight at 4° C. The bound primary antibodies were detected using appropriate horseradish peroxidase-conjugated secondary antibodies followed by detection with enhanced chemiluminescence (Perkin Elmer, Wellesley, Mass.). For successive blotting, the membranes were treated with stripping buffer (Chemicon, CA) for 15 minutes and then re-analyzed using appropriate antibodies.

Cytotoxicity Assays. Cell growth inhibition was determined by 3-(4,5-dimethylthiazol-2-yl)-2,5-diphenyltetrazolium (MTT) bromide assay using MTT (Sigma Chemicals, St. Louis, Mo.) reagent in 96-well plates. Briefly, approximately $1\times10^4$ cells were plated in 96-well plate and 24 hours later paclitaxel was added in appropriate concentrations. After 72 hours of drug incubation, 50 μl of MTT reagent was added to each well and incubated for an additional 4 hours. 200 μl of isopropanol-HCl solution was added to each well to dissolve the cell pellets. Absorbance was determined using a 96-well SpectraMax plate reader (Molecular Devices, Sunnyvale, Calif.) at 570 nm.

In vitro Transfection with Si RNA: The human prohibitin mRNA-specific RNA oligonucleotides and human GST-π mRNA-specific oligonucleotides were purchased as SmartPool mixtures (combinations of four different oligonucleotides) from Dharmacon (Lafayette, Colo.). A non-specific scrambled RNAi duplex was used as a negative control, 2.5× 104 cells were seeded in 24 well dishes 1 day prior to transfection. Cells were transfected with the appropriate siRNA's using SilentFect (Biorad) reagent according to manufacturers protocol (con fluency 50%-70% at the time of transfection). The transfection mixture was prepared by mixing 625 μl of serum-free medium containing 8 μl of 20 μM siRNA with 625 μl of serum-free media containing 18 μl of SilentFect reagent. Before transfection, the medium in the 24 wells was replaced with 250 μl of fresh medium. The control siRNA mixture was prepared by mixing 625 μl of serum-free medium containing 3 μl of 50 μM control siRNA with 625 μl serum-free medium containing 18 μl of SilentFect reagent. The transfection mixture (50 μl) was added to the 24-well plate within 20 min after mixture preparation in a total volume of 300 μl (final concentration of 20 nM siRNA). The cells were incubated for 4 h at 37° C., after which the medium in the 24-well plate was replaced with 300 μl of fresh medium. Cells were treated with control medium or with paclitaxel at 10 μM or 100 nM 24 h after transfection with specific siRNA or control siRNA as described above. Cells were counted for cell number and harvested for western blotting 72 h after paclitaxel treatment. Effect of paclitaxel on siRNA treated cells was computed as % cell survival.

Immunofluorescence and Confocal Microscopy:

Cells were seeded on round glass coverslips coated with 10 μg/ml fibronection (BD Biosciences) in 24 well plates. Cells were stained for mitochondria either with 400 nM Mitotracker Red, a live-cell stain for mitochondria or with antibodies to VDAC (Abcam, Cambridge, Mass.) a mitochondrial porin channel protein located on the outer membrane of the mitochondria. Cells were incubated for 45 min at 37° C. in medium containing 400 nM of Mitotracker. The medium was removed, and the cells washed with prewarmed media. Cells were fixed with 4% paraformaldehyde for 10 min at room temperature and permeabilized with ice-cold acetone for 5 min at room temperature. Cells were then washed with PBS and blocked for 30 min in PBS containing 1% BSA. Cells were then stained for prohibitin by first incubating them in PBS containing 1% BSA and rabbit anti-prohibitin (1:100) for 1 h at room temperature followed by Alexa green 488 conjugated anti-rabbit IgG for 30 min in dark. The cells were then rinsed with PBS, followed by distilled water. The resulting coverslips were mounted on glass slides with Vectashield Mounting media containing DAPI (Burlingame, Calif.). The cells were analyzed using a Leica (Bannockburn, Ill.) DMIRE2 SP2 confocal microscope equipped with an Acousto-Optical Beam Splitter (AOBS) and X 40 oil immersion objective operated with differential interference contrast (DIC) and fluorescence. Fluorescence was excited sequentially; first by a 488-nm line of an argon-krypton laser with a recorded emission from 500 to 572 nm, and then by a 543-nm line of a Helium Neon Laser recorded emission from 613 to 700 nm.

Results

Protein Profiling by Two-Dimensional Gel Electrophoresis and Mass Spectrometry Identifies Proteins Associated with Paclitaxel Resistance We adopted a proteomics based approach using two-dimensional gel electrophoresis coupled with mass spectrometry to identify novel proteins associated with paclitaxel resistance. Two different cancer cell lines were used in the study; 1) a paclitaxel-sensitive lung cancer cell line (A549) and its paclitaxel-resistant variant (A549-TR) (Chou Cancer Res 2005), 2) a uterine sarcoma cell line (MES-SA) and its paclitaxel-resistant variant (MES-SA/DX5). The resistant sublines differed from the parental lines in their sensitivity to paclitaxel by greater than 100-fold (FIGS. 1A and B). Cytoplasmic and, microsomal fractions from the parental and paclitaxel-resistant sublines were prepared, as described in materials and methods and separated by two-dimensional gel electrophoresis. The purpose of this fractionation step was to enable identification of low-abundant proteins that would otherwise be undetected in total protein lysates as well as to detect possible translocations of proteins from one site to another. Analysis of the gels revealed more than 50 proteins differentially expressed between A549 (parental) and A549-TR (paclitaxel-resistant) cell lines. Examination of the respective fractions from the MES-SA (parental) and MES-SA-DX5 (paclitaxel-resistant) cells also revealed multiple differentially expressed proteins.

Importantly, we observed a limited number of proteins that were differentially expressed in both paclitaxel-resistant cell models. Comparison of A549 and A549TR, MES-SA and MES-SA DX5 two-dimensional gels of cytoplasmic fractions using computer imaging software (PDQuest) analysis revealed the same protein is overexpressed in the Paclitaxel resistant sublines of both cell types compared to their parental cells (data not shown). Tandem-mass spectrometry was used to identify the protein as glutathione-S-tranferase-Pi GST-π. Several other proteins including Tubulin β-5, and annexin I, were found to be overexpressed in the cytoplasmic fraction of the resistant cell lines, while lipocortin was relatively under-represented in this fraction (TABLE 2).

Comparison of the A549 and A549TR, MES-SA and MES-SA DX5 two-dimensional gels using computer software (PDQuest) analysis revealed the same protein is overexpressed in the paclitaxel resistant sublines of both cell types compared to their parental lines. Tandem-mass spectrometry was used to identify the protein as Prohibitin (data not shown). Prohibitin, a protein not previously associated with taxane resistance, was consistently overexpressed in the microsomal fractions of the resistant cell lines. GST-π, representative of a cytoplasmic fraction protein, and prohibitin, representative of a microsomal fraction protein, were chosen for further investigation of their role in paclitaxel-resistance.

Validation of Prohibitin and GST-π Protein Expression

Figure 2A:
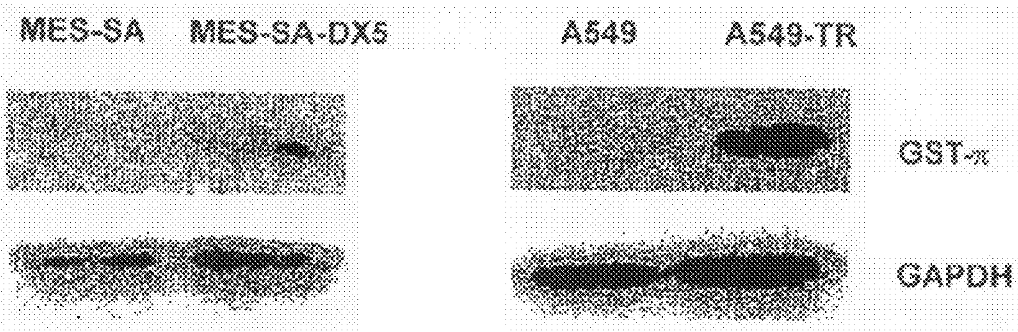
FIGS. 2A to 2D show Western blot analysis of protein fractions and whole cell lysates.
Figure 2B:
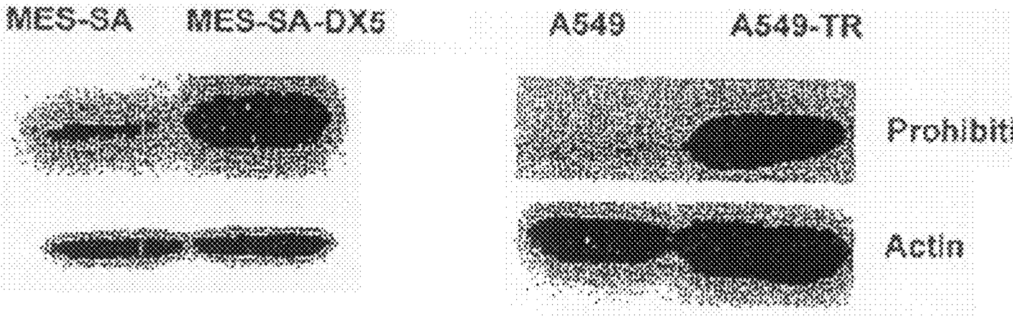
Figures 2C, 2D:
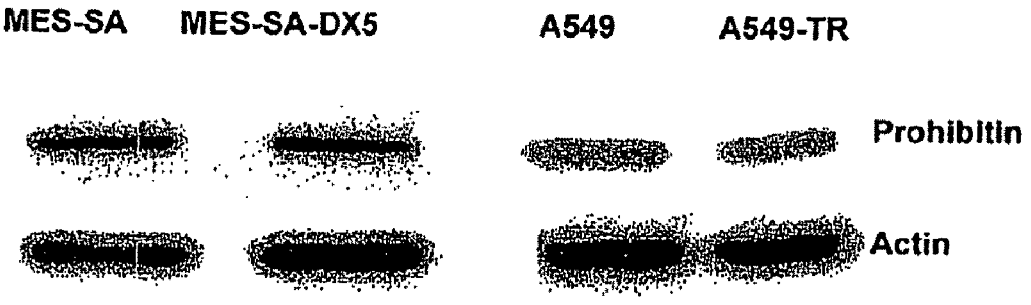

GST-7 and prohibitin protein levels were examined in whole cell lysates and cellular fractions by Western blot analysis. Increased levels of GST-π were seen in the cytoplasmic fractions (FIG. 2A) and in whole cell lysates (FIG. 2C) of both resistant cell lines. Although increased levels of prohibitin were seen in microsomal fractions (FIG. 2B) of resistant cells, confirming the two-dimensional gel analysis, there was no difference in the total amount of prohibitin protein seen in whole cell lysates (FIG. 2D). This is an intriguing result as prohibitin has been shown to migrate between intracellular locales, thus the intracellular distribution of prohibitin is relevant to the resistant phenotype.

Cellular Localization of Prohibitin:

The potential differential localization of prohibitin in paclitaxel-resistant cell lines was further investigated using confocal microscopy. In both parental (sensitive) cell lines, A549 and MES-SA, prohibitin staining was predominantly perinuclear (data not shown), and colocalization determined. Interestingly, the paclitaxel-resistant cells (A549-TR and MES-SA-DX), displayed reduced staining with MitoTracker Red relative to parental cells and both MitoTracker Red and prohibitin staining was distributed throughout the cell rather than localized to the perinuclear region with fewer overlapping regions of co-localization (data not shown). Similar results were obtained using a polyclonal antibody against prohibitin and a monoclonal antibody against the mitochondrial protein VDAC/Porin (data not shown). Prohibitin staining co-localized with the live mitochondrial stain MitoTracker Red in the parental cells (data not shown), suggesting a mitochondrial localization for prohibitin in the paclitaxel sensitive cell lines which was less apparent in the resistant cells (data not shown). Thus paclitaxel-resistance in these cells is associated with prohibitin relocalization.

We further investigated whether differences in cell surface prohibitin were apparent on placlitaxel-resistant cells. Prohibitin immunostaining was performed on non-permeabilized cells. Relative to control A549 cells, increased surface staining was observed on the paclitaxel-resistant A549TR (data not shown). Accordingly, cell-surface prohibitin is an important therapeutic target for the development of new drugs for the treatment of taxane-resistant tumors.

Effect of Silencing GST-π and Prohibitin on Paclitaxel Sensitivity

Figure 3A:
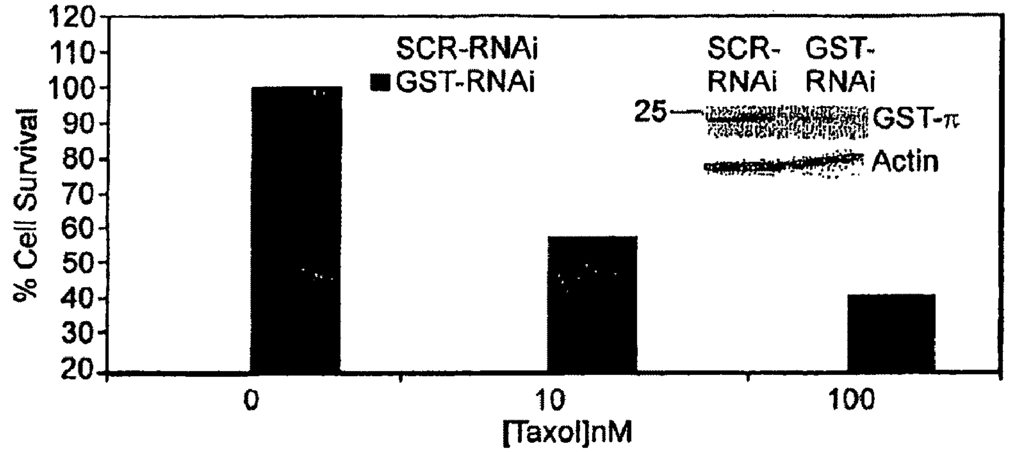
FIGS. 3A and 3B show bar graphs depicting the effect of silencing GST-N and prohibitin individually on paclitaxel sensitivity.
Figure 3B:
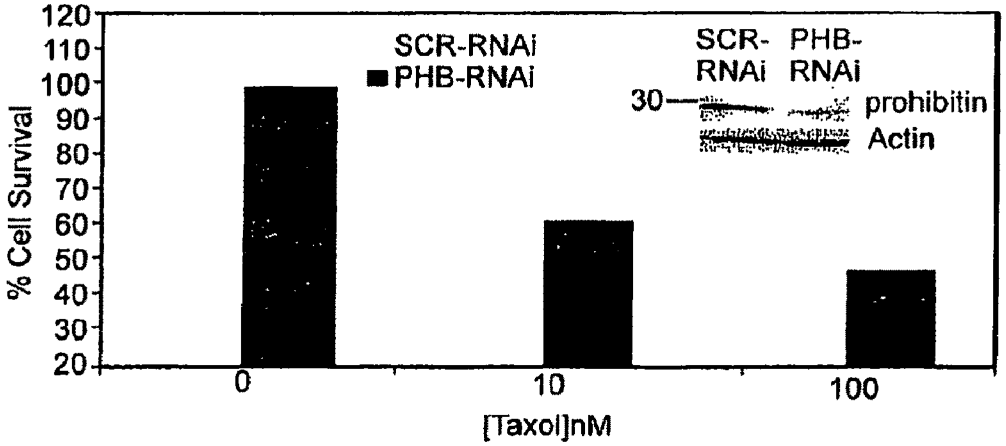
Figure 4A:
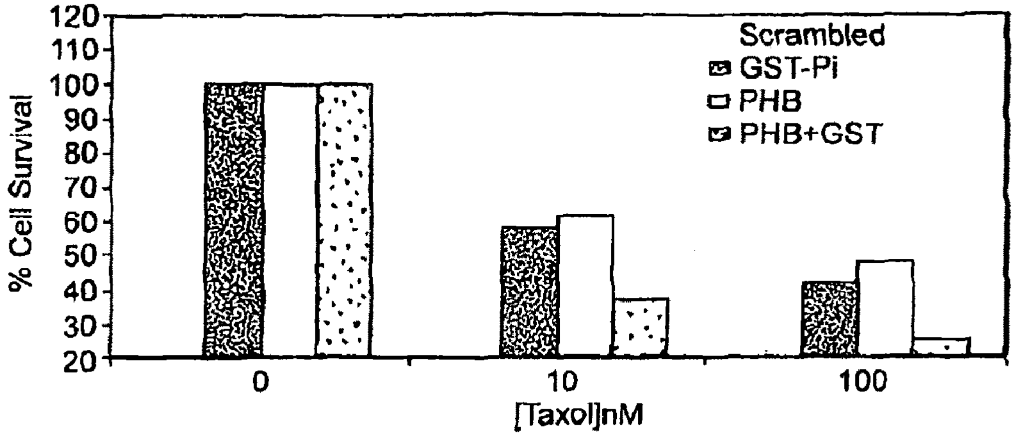
FIGS. 4A and 4B how bar graphs depicting the effect of combined silencing of GST-π and prohibitin using siRNA on paclitaxel sensitivity of resistant cells.
Figure 4B:
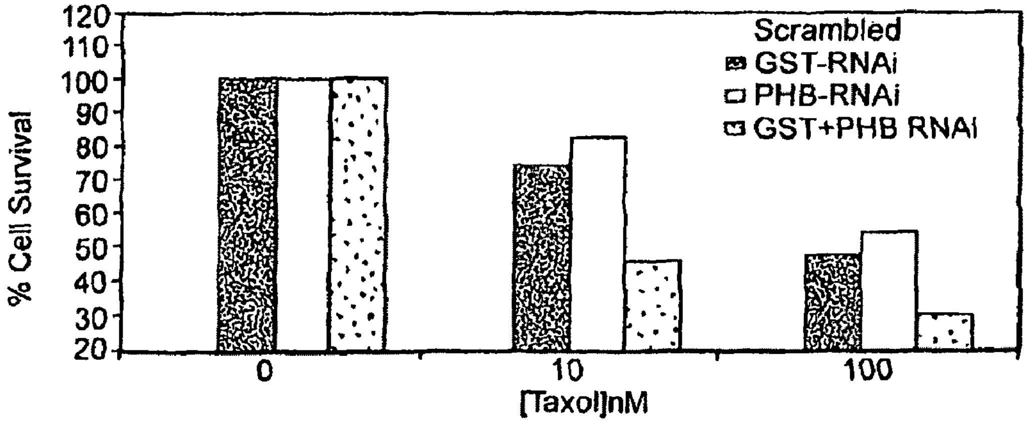

To determine the functional significance of the protein changes that were correlated with paclitaxel-resistance, we employed SiRNA (Dharmacon Smart Pools) to selectively reduce the amounts of these proteins in resistant cell lines. Conditions were chosen in which the protein levels were reduced by 50-70% for GST-71 and prohibitin (FIGS. 3A and 3B insert respectively). Scrambled, non-specific siRNA had no effect on protein levels. Knockdown of either GST-π (FIG. 3A) or prohibitin (FIG. 3B) expression in the A549TR cells decreased cell survival by 24% and 20% respectively when the cells were challenged with 10 nM paclitaxel. Similar results were obtained using a single prohibitin siRNA (21mer) oligonucleotide (Dharmacon) suggesting that the increase in paclitaxel sensitivity is not due to possible off-target effects (data not shown). Intriguingly, simultaneous transfection with GST-π siRNA and prohibitin siRNA smart-pools in the A549TR (FIG. 4A) and MES-SA-DX5 cells (FIG. 4B) dramatically decreased cell survival after exposure to 10 nM paclitaxel relative to control siRNA. Again similar results were obtained using the single prohibitin siRNA (21mer) oligonucleotide (Dharmacon) (data not shown). These results suggest that combined suppression of prohibitin along with GST-π can effectively reverse paclitaxel resistance and render resistant cells sensitive to the drug.

In this study we used a proteomics approach to identify proteins whose level of expression or cellular location are associated with resistance to the antitumor drug paclitaxel. The detection of changes in PV-tubulin and GST-π serve as a "proof of principle" for our proteomics based approach, as both proteins have previously been implicated in paclitaxel-resistance in several different studies. Paclitaxel binds to the β-subunit of tubulin, of which at least seven isotypes exist at the protein level in humans. These can be classified into two distinct groups: (1) βI-, βII-, βIVa- and βIVb-tubulin and (2)

βIII-, βV-, and βVI-tubulin. Tumor cells often express a different complement of β-tubulin isotypes than their normal counterparts. Overexpression, mutation, and post-translational modifications of β-tubulin have all been implicated in paclitaxel resistance in cell lines and tumors. Kavallaris et. al. (Br J Ca 1999) showed that paclitaxel-resistant A549 cells overexpressed βIII-tubulin and that partial sensitivity to paclitaxel was regained by down-regulation of βIII-tubulin in these cells. More recently it has been shown that overexpression of βIII-tubulin induces paclitaxel resistance by reducing the ability of paclitaxel to suppress microtubule dynamics (Kamath JBC 2005). Bhattacharya and Cabral showed that mouse PV-tubulin overexpression in CHO cells results in profound microtubule disorganization and dependence of cells on paclitaxel for growth (14) and more recently Verdier-Pinard et. al. were able to detect βV-tubulin protein in human cell lines and found that it is highly expressed in Hey, an epithelial ovarian cancer cell line. (Pascal Verdier-Pinard, Biochem 2005). Except for their C-termini, βIII- and, βV-tubulin sequences are closely related. It is not surprising therefore that we identified βV-tubulin as one of the proteins overexpressed in the paclitaxel-resistant cell lines.

Increased levels of GST-β have also been associated with taxane resistance. GST-π is a detoxification enzyme frequently upregulated in tumors and its expression correlates with anticancer drug resistance, especially resistance to alkylating agents such as cisplatin and doxorubicin. GST-π has also been shown to be a prognostic indicator of drug response and survival in non-small cell lung cancer and breast cancer. Clinical studies using TLK286, a GST-π-activated glutathione analog prodrug, in platinum and paclitaxel refractory or resistant ovarian cancer are currently in progress. (Kavanagh J J et. al. Int J Gynecol Cancer. 2005). Our experiments now show that silencing GST-β partially restores paclitaxel sensitivity in two cellular models of drug resistance. These results provide a direct demonstration of the utility of GST-π suppression in sensitizing resistant cells to the effects of paclitaxel.

We also present the novel finding of cell surface expression of prohibitin in paclitaxel-resistant cells. At least two related proteins, prohibitin, (Phb-1, BAP32) and Phb2 (BAP37, prohibitone, REA) exist in eukaryotic cells. Prohibitins are well characterized as mitochondrial chaperone proteins that function in a high-molecular-weight complex in the inner membrane to maintain mitochondrial integrity. However, their role outside the mitochondria remains controversial. Mammalian prohibitins have been detected in the cytosol and the nucleus and postulated to play a role in tumor suppression, inhibition of proliferation, and apoptosis. Prohibitins have also recently been found in the plasma membrane of intestinal epithelial cells (Sharma PNAS 2004) and the vasculature of white adipose tissue (Kolonin M G et al 2004 Nat. Med.). As we also find prohibitin on the surface of paclitaxel-resistant cells, prohibitin can function as a surface-binding site that will be a useful target for therapeutic compounds. Our results further indicate that the cellular location of prohibitin is altered in paclitaxel-resistant cells relative to their drug-sensitive parent cell lines even though the total levels of prohibitin are not altered in the resistant cell lines. Prohibitin silencing reduces the overall levels of prohibitin and results in partial reversal of the resistant phenotype. Unexpectedly, combined reduction of both prohibitin and GST-π results in near complete restoration of paclitaxel sensitivity in vitro. This approach is useful in sensitizing cancer patients whose tumors show resistance to these commonly used drugs.

Briefly, we have seen that in the parental cells (A549 and MES-SA) prohibitin is primarily localized in the mitochondria (See Table 1 for a description of resistance). In the Taxoid family member resistant variants (A549TR and MES-SA DX) prohibitin is diffused all over the cell. We have further found that elevated levels of prohibitin is present in the cell surface of the Taxoid family member resistant cells than in the parental cells.

We have further shown that antagonizing prohibitin and GST-π in combination by simultaneously using siRNA against their mRNA in the drug resistant sublines reverses their paclitaxel resistance significantly.

TABLE 1

| Parental Cell Line | Drug Resistant Cell Line | Resistance Raised Against | Cross Resistance |
|---|---|---|---|
| Lung Cancer (A549) | Lung Cancer (A549TR) | Taxol | Multiple drug resistant (MDR) |
| Uterine Sarcoma (MES-SA) | Uterine Sarcoma (MES-SA DX) | Doxorubicin | Multiple Drug Resistant (MDR) Taxol |

TABLE II

| Proteins Identified in both A549TR and MES-SA DX5 Cells | Expression Pattern | Cellular Fraction |
|---|---|---|
| Glutathione-S-Transferase-pi | Overexpressed | Cytoplasm |
| Prohibitin | Overexpressed | Microsomal |
| Tubulin β-5 | Overexpressed | Cytoplasm |
| Annexin I | Overexpressed | Cytoplasm |
| Lipocortin | Underexpressed | Microsomal |

All references cited herein are incorporated herein in their entirety by reference.

REFERENCES

1, Wani J. Am. Chem. Soc., 93: 2325-2327, 1971.
2. Rowinsky, E. K. The development and clinical utility of the taxane class of antimicrotubule chemotherapy agents. Annu Rev Med, 48: 353-374, 1997.
3. Holmes, F. A., Walters, R. S., Theriault, R. L., Forman, A. D., Newton, L. K., Raber, M. N., Buzdar, A. U., Frye, D. K., and Hortobagyi, G. N. Phase II trial of taxol, an active drug in the treatment of metastatic breast cancer. J Natl Cancer Inst, 83: 1797-1805, 1991.
4. McGuire, W. P., Rowinsky, E. K., Rosenshein, N. B., Grumbine, F. C., Ettinger, D. S., Armstrong, D. K., and Donehower, R. C. Taxol: a unique antineoplastic agent with significant activity in advanced ovarian epithelial neoplasms. Ann Intern Med, 111: 273-279, 1989.
5. Abal, M., Andreu, J. M., and Barasoain, I. Taxanes: microtubule and centrosome targets, and cell cycle dependent mechanisms of action. Curr Cancer Drug Targets, 3: 193-203, 2003.
6. Checchi, P. M., Nettles, J. H., Zhou, J., Snyder, J. P., and Joshi, H. C. Microtubule-interacting drugs for cancer treatment. Trends Pharmacol Sci, 24: 361-365, 2003.
7. Wilson, L. and Jordan, M. A. New microtubule/tubulin-targeted anticancer drugs and novel chemotherapeutic strategies. J Chemother, 16 Suppl 4: 83-85, 2004.
8. Gottesman, M. M., Fojo, T., and Bates, S. E. Multidrug resistance in cancer: role of ATP-dependent transporters. Nat Rev Cancer, 2: 48-58, 2002.
9. Dumontet, C. and Sikic, B. I. Mechanisms of action of and resistance to antitubulin agents: microtubule dynamics, drug transport, and cell death. J Clin Oncol, 17: 1061-1070, 1999.

10. Giannakakou, P., Sackett, D. L., Kang, Y. K., Zhan, Z., Buters, J. T., Fojo, T., and Poruchynsky, M. S. Paclitaxel-resistant human ovarian cancer cells have mutant beta-5-tubulins that exhibit impaired paclitaxel-driven polymerization. J Biol Chem, 272: 17118-17125, 1997.

11. Gonzalez-Garay, M. L., Chang, L., Blade, K., Menick, D. R., and Cabral, F. A beta-5-tubulin leucine cluster involved in microtubule assembly and paclitaxel resistance. J Biol Chem, 274: 23875-23882, 1999.

12. Kavallaris, M., Kuo, D. Y., Burkhart, C. A., Regl, D. L., Norris, M. D., Haber, M., and Horwitz, S. B. Taxol-resistant epithelial ovarian tumors are associated with altered expression of specific beta-5-tubulin isotypes. J Clin Invest, 100: 1282-1293, 1997.

13. Bhattacharya, R. and Cabral, F. A ubiquitous beta-5-tubulin disrupts microtubule assembly and inhibits cell proliferation. Mol Biol Cell, 15: 3123-3131, 2004.

14. Blagosklonny, M. V. and Fojo, T. Molecular effects of paclitaxel: myths and reality (a critical review). Int J Cancer, 83: 151-156, 1999.

15. Miller, T. P., Grogan, T. M., Dalton, W. S., Spier, C. M., Scheper, R. J., and Salmon, S. E. P-glycoprotein expression in malignant lymphoma and reversal of clinical drug resistance with chemotherapy plus high-dose verapamil. J Clin Oncol, 9: 17-24, 1991.

16. Boekhorst, P. A., van Kapel, J., Schoester, M., and Sonneveld, P. Reversal of typical multidrug resistance by cyclosporin and its non-immunosuppressive analogue SDZ PSC 833 in Chinese hamster ovary cells expressing the mdr1 phenotype. Cancer Chemother Pharmacol, 30: 238-242, 1992.

17. Masanek, U., Stammler, G., and Volm, M. Messenger RNA expression of resistance proteins and related factors in human ovarian carcinoma cell lines resistant to doxorubicin, taxol and cisplatin. Anticancer Drugs, 8: 189-198, 1997.

The invention claimed is:

1. A method for predicting the resistance of a tumor in a subject to a member of the taxoid family, the method comprising:

(a). measuring a level of cell surface prohibitin in a tumor sample obtained from the subject;

(b). comparing the level measured in step (a) to a standard level of cell surface prohibitin; and (c) identifying the tumor in the subject as resistant to a member of the taxoid family when the measured level of cell surface prohibitin in the tumor sample is increased relative to the standard level of cell surface prohibitin.

2. The method of claim 1, wherein the subject had been treated with the member of the taxoid family.

3. The method of claim 1, wherein the member of the taxoid family is paclitaxel or docetaxel.

4. A method for predicting the resistance of a tumor in a subject to a member of the taxoid family, the method comprising:

(a). measuring the level of cell surface prohibitin in multiple tumor samples obtained from the subject periodically over a period time; and (b). measuring a change in the measured level of cell surface prohibitin in the tumor samples, wherein an elevation of the level of cell surface prohibitin in the tumor samples over the period of time is indicative of resistance of the tumor to a member of the taxoid family.

5. The method of claim 4, wherein the subject had been treated with the member of the taxoid family.

6. The method of claim 4, wherein the member of the taxoid family is paclitaxel or docetaxel.

7. A method for improving the effectiveness of tumor treatment in a subject comprising:

measuring the level of cell surface prohibitin in a tumor sample obtained from the subject, and identifying the tumor in the subject as resistant to a member of the taxoid family when if the measured level of cell surface prohibitin in the tumor sample is elevated as compared to a standard level of cell surface prohibitin indicates that the subject is in need of alternative treatment so as to improve the effectiveness of tumor treatment.

8. The method of claim 7, wherein the subject had been treated with the member of the taxoid family.

9. The method of claim 8, wherein the member of the taxoid family is paclitaxel or docetaxel.

* * * * *

UNITED STATES PATENT AND TRADEMARK OFFICE

CERTIFICATE OF CORRECTION

PATENT NO. : 8,148,086 B2
APPLICATION NO. : 12/085125
DATED : April 3, 2012
INVENTOR(S) : Bruce R. Zetter et al.

It is certified that error appears in the above-identified patent and that said Letters Patent is hereby corrected as shown below:

On the Title Page, the assignee information should read:

(73) Assignee: Children's Medical Center Corporation, Boston, MA (US)

In the Claims:

Claim 7, column 32 at lines 27-36, should read:

7. A method for improving the effectiveness of tumor treatment in a subject comprising:

measuring the level of cell surface prohibitin in a tumor sample obtained from the subject, and identifying the tumor in the subject as resistant to a member of the taxoid family when the measured level of cell surface prohibitin in the tumor sample is elevated as compared to a standard level of cell surface prohibitin which indicates that the subject is in need of alternative treatment so as to improve the effectiveness of tumor treatment.

Signed and Sealed this
Twenty-ninth Day of May, 2012

David J. Kappos
*Director of the United States Patent and Trademark Office*